(12) United States Patent
Katayama et al.

(10) Patent No.: US 7,639,865 B2
(45) Date of Patent: Dec. 29, 2009

(54) IMAGE PROCESSING APPARATUS, IMAGE PROCESSING METHOD, COMPUTER READABLE MEDIUM, AND COMPUTER PROGRAM THEREOF

(75) Inventors: Eisaku Katayama, Tokyo (JP); Norio Baba, Tokyo (JP)

(73) Assignee: Toudai TLO, Ltd., Tokyo (JP)

( * ) Notice: Subject to any disclaimer, the term of this patent is extended or adjusted under 35 U.S.C. 154(b) by 655 days.

(21) Appl. No.: 10/461,920

(22) Filed: Jun. 13, 2003

(65) Prior Publication Data
US 2004/0041806 A1    Mar. 4, 2004

(51) Int. Cl.
*G06K 9/00* (2006.01)
(52) U.S. Cl. .................................... 382/154
(58) Field of Classification Search ................ None
See application file for complete search history.

(56) References Cited

U.S. PATENT DOCUMENTS

| 5,414,261 | A | * | 5/1995 | Ellisman et al. | 250/311 |
| 5,841,894 | A | * | 11/1998 | Horie | 382/154 |
| 6,075,605 | A | * | 6/2000 | Futamura et al. | 356/608 |
| 6,128,405 | A | * | 10/2000 | Fujii | 382/154 |
| 6,160,908 | A | * | 12/2000 | Hakozaki | 382/154 |
| 6,418,243 | B1 | * | 7/2002 | Skoglund et al. | 382/274 |
| 6,531,697 | B1 | * | 3/2003 | Nakamura et al. | 250/311 |
| 6,621,921 | B1 | * | 9/2003 | Matsugu et al. | 382/154 |
| 6,980,937 | B2 | * | 12/2005 | Hayes | 703/2 |
| 2004/0114806 | A1 | * | 6/2004 | Katayama et al. | 382/218 |

FOREIGN PATENT DOCUMENTS

| JP | 62-219075 | 9/1987 |
| JP | 4-70983 | 3/1992 |

(Continued)

OTHER PUBLICATIONS

Patent Abstracts of Japan, Publication No. 04-070983 dated Mar. 5, 1992, 1 pg.

(Continued)

*Primary Examiner*—Matthew C Bella
*Assistant Examiner*—Alex Liew
(74) *Attorney, Agent, or Firm*—Osha · Liang LLP

(57) ABSTRACT

It is an object of the present invention to acquire 3-dimensional image data that correctly express a structural configuration of the subject by processing the projected image data obtained by projecting the subject toward the plural angles. A shape computing unit 260 calculates shape data which represent a outline of the subject, using a plurality of 1st image data of the subject obtained by projecting the subject toward the plural angles. A distributing unit 220 generates gray-scale density-distributions by spreading and distributing densities shown in gray-scale image of the subject respectively within angles along which said gray-scale image was captured. A second integrating unit 240 generates 3-dimensional gray-scale data, which expresses the subject with the 3-dimensional image data, by integrating a plurality of said gray-scale density-distributions generated from a plurality of gray-scale image captured from a plurality of angles. A first integrating unit 280 integrates the shape data and 3-dimensional gray-scale image. A data processing unit 300 generates 3-dimensional image data by extracting only density that exists in perimeter of a shape that the shape data represent, from the 3-dimensional gray-scale data.

29 Claims, 13 Drawing Sheets

FOREIGN PATENT DOCUMENTS

JP          8-292164          11/1996

OTHER PUBLICATIONS

Patent Abstracts of Japan, Publication No. 62-219075 dated Sep. 26, 1987, 1 pg.

Patent Abstracts of Japan, Publication No. 08-292164 dated Nov. 5, 1996, 1 pg.

International Preliminary Examination Report issued in International Application No. PCT/JP01/10777 mailed Oct. 30, 2002, 4 pages.

International Search Report issued in International Application No. PCT/JP01/10777 mailed Feb. 12, 2002, 2 pages.

Office Action mailed Jun. 1, 2004 in Japanese Patent Application No. 2002-550599 (2 pages), with translation (3 pages).

Patent Abstracts of Japan, Publication No. 04-070983 dated Mar. 5, 1992, 2 pgs.

Patent Abstracts of Japan, Publication No. 62-219075 dated Sep. 26, 1987, 2 pgs.

Patent Abstracts of Japan, Publication No. 08-292164 dated Nov. 5, 1996, 2 pgs.

English Translation of International Preliminary Examination Report dated Oct. 30, 2002 (5 pgs.).

English Translation of Taiwanese Office Action citing references B1 and B2 (undated) (2 pgs.).

Taiwan Publication No. 411269; Publication Date: Nov. 11, 2000; "X-Ray CT Apparatus and Image Diagnostic Apparatus" (28 pgs.).

Taiwan Publication No. 352336; Publication Date: Feb. 11, 1999; "Improved Method of and Apparatus for Helical Computed Tomography Scanning With Asymmetric Detector System"; (51 pgs.).

* cited by examiner

IMAGE PROCESSING APPARATUS, IMAGE PROCESSING METHOD, COMPUTER READABLE MEDIUM, AND COMPUTER PROGRAM THEREOF

This present application claims priority from a Japanese Patent Application No. 2000-381636 filed on Dec. 15, 2000, and a Japanese Patent Application No. 2001-120262 filed on Apr. 18, 2001, the contents of which are incorporated herein by reference.

BACKGROUND OF THE INVENTION

Structure of a subject along an image-capturing direction, that is, information along a depth direction, cannot be acquired only by one projected image obtained by a transmission electron microscope and the like. In this case, information along the depth direction of the subject can be acquired by spreading gray scale intensities of a plurality of projected images captured from a plurality of angles within the image-captured angles, integrating them together, and examining the integration thereof.

However, by a simple integration of gray-scale intensities of a plurality of projected images, which was captured from a plurality of angles and spread within the image-captured angles, integrations of the gray-scale intensities may arise at the positions where the subject originally did not exist, to give false information, which shows as if the subject existed there. Conventionally, it was difficult to suppress or remove the above-described false information. Accordingly, it was impossible to acquire 3-dimensional image data that correctly express the structural configuration of the subject by processing the projected image data obtained by projecting the subject toward the plural angles.

SUMMARY OF THE INVENTION

Therefore, it is an object of the present invention to provide an image processing apparatus, an image processing method, a computer readable medium, and a computer program thereof, which are capable of overcoming the above drawbacks accompanying the conventional art. This object is achieved by combinations described in the independent claims. The dependent claims define further advantageous and exemplary combinations of the present invention.

According to the first aspect of the present invention, an image processing apparatus for acquiring 3-dimensional data regarding a structural configuration of a subject by processing image data of the subject is provided. The image processing apparatus includes a shape computing unit which calculates shape data which represent an outline of the subject, using a plurality of 1st image data of the subject obtained by projecting the subject toward the plural angles, a first integrating unit which integrates the shape data and the gray-scale image of the subject acquired by a projection-type image-capturing apparatus.

The image processing apparatus may further include a distributing unit which generates gray-scale density-distributions by spreading and distributing densities shown in the gray-scale image respectively within angles along which the gray-scale image was captured, and a second integrating unit which generates 3-dimensional gray-scale data, which expresses the subject with 3-dimensional image data, by integrating a plurality of the gray-scale density-distributions generated from a plurality of the gray-scale image captured from a plurality of angles, wherein the first integrating unit integrates the shape data and the 3-dimensional gray-scale data by the second integrating unit. In this case, the image processing apparatus may further include a data processing unit which generates 3-dimensional image data by extracting only density, which exists in perimeter of the shape that the shape data represent, from the 3-dimensional gray-scale data.

The image processing apparatus may further include a gray-scale density data-generating unit which calculates the gray-scale image which should be acquired when the subject was captured from a different angle from the plurality of the above angles, from the above 3-dimensional image data.

The image processing apparatus may further include a sampling unit which extracts respectively gray-scale image of a plurality of the subjects facing a plurality of angles, included in a single gray-scale image acquired by the projection-type image-capturing apparatus, wherein the first integrating unit may use a plurality of the gray-scale image which the sampling unit extracted.

The subject may constitutes substance which has a helical symmetry, the apparatus dealing with gray-scale image of the substance as the above single gray-scale image, further including an angle computing unit which obtains a reference angle which the single subject as a reference faces, and further calculates angles which each of the subjects faces by adding or subtracting the angle by which the helix rotates by the single subject, from the reference angle.

The second aspect of the present invention provides an image processing apparatus for acquiring 3-dimensional data regarding a structural configuration of a subject by processing image data of the subject, is provided. The image processing apparatus includes a shape computing unit which calculates shape data which represent an outline of the subject, using a plurality of 1st image data of the subject obtained by projecting the subject toward the plural angles, and an image data generating unit which generates 3-dimensional image data by distributing density of the gray-scale image of the subject acquired by a projection-type image-capturing apparatus, around the outline.

The image processing apparatus may further include a gray-scale density data-generating unit which calculates the gray-scale image which should be acquired when the subject was captured from a different angle from the plurality of the above angles, from the above 3-dimensional image data.

The image processing apparatus may further include a sampling unit which extracts respectively gray-scale images of a plurality of the subjects facing a plurality of angles, included in a single gray-scale image acquired by the projection-type image-capturing apparatus, wherein the image data generating unit may use a plurality of the gray-scale images which the sampling unit extracted.

The subject may constitutes substance which has a helical symmetry, while the apparatus deals with data gray-scale image of the substance as the single gray-scale image, further including an angle computing unit which calculates an angle which the single subject as a reference faces, further calculating angles which each of the subjects faces by adding or subtracting the angle which the helix rotates by the single subject, from the reference angle.

Moreover, in the $1^{st}$ and $2^{nd}$ aspect of the present invention, the gray-scale image may be image data acquired by a transmission electron microscope. An image data of the pattern of the subject may be used as the first image data.

The shape computing unit may include a position relating unit which relates positions of processing objective points in the subject in a 1st and 2nd images which are consecutive in the order of angle, and relates the positions of the processing objective points in the 2nd image and a 3rd image, a height data computing unit which calculates height data for representing height of the position of the processing objective point using two sets of position relations by the position relating unit, and a shape data computing unit which generates the shape data of the subject using the height data of a plurality of the processing objective points by the height data computing unit, wherein the apparatus calculates the shape data using three or more of the first images. In this case, the 1st, 2nd, and 3rd images may be images captured with a rotation of the subject by a predetermined angle with a same rotation axis as the rotation center, and the height data computing unit may calculate the height data using the predetermined angle. Besides, the 1st and 2nd image may be images captured with a rotation of the subject by a predetermined angle with a first rotation axis as the rotation center, and the 3rd image may be an image captured with a rotation of the subject by the predetermined angle from the position where the 1st image was captured, with another rotation axis as the rotation center, and the height data computing unit may calculate the height data using the predetermined angle. The position relating unit may calculate distances from a base line defined in advance in the subject to each of the processing objective points in the image, and re-detects positions of the processing objective points in the 1st and 2nd images, when a difference of the distance in the 1st and 2nd images is more than a predetermined value, and relates again the processing objective points in the 2nd and 3rd images when a difference of the distance in the 2nd and the 3rd images is more than a predetermined value. The height data computing unit may calculate the height data by a least-squares error method with height data of the 1st and 2nd images and height data by the 2nd and 3rd images. Further to this case, the position relating unit may re-detect the positions of the processing objective points, when a error by the least-squares error method is more than a predetermined value.

The third aspect of the present invention provides an image processing method for acquiring 3-dimensional data of a subject by processing image data of the subject. The image processing method includes steps of calculating shape data which represent an outline of the subject, using a plurality of 1st image data of the subject obtained by projecting the subject toward the plural angles, generating gray-scale density-distributions by spreading and distributing densities, shown in gray-scale image of the subject acquired by a projection-type image-capturing apparatus, respectively within angles along which the gray-scale image was captured, generating 3-dimensional gray-scale data, which expresses the subject with 3-dimensional image data, by integrating a plurality of the gray-scale density-distributions generated from a plurality of the gray-scale image captured from a plurality of angles, integrating the shape data and the 3-dimensional gray-scale data, and generating 3-dimensional image data by extracting only density which exists in perimeter of the outline which the shape data represent, from the 3-dimensional gray-scale data.

The image processing method may further includes steps of extracting gray-scale image of a plurality of the subjects facing a plurality of angles from a single gray-scale image acquired by the projection-type image-capturing apparatus, and generating the gray-scale density-distributions using the extracted gray-scale image. In this case, the subject may constitute substance which has a helical symmetry, while the apparatus deals with gray-scale image of the substance as the single gray-scale image. The image processing method may further include steps of recognizing a reference angle, which is an angle the single subject as a reference faces, and calculating angles which each of the subjects faces by adding or subtracting the angle which the helix rotates by the single subject from the reference angle.

The forth aspect of the present invention provides an image processing method for acquiring 3-dimensional data of a subject by processing image data of the subject. The image processing method includes steps of calculating an outline of the subject, using a plurality of 1st image data of the subject obtained by projecting the subject toward the plural angles, and generating 3-dimensional image data by distributing density of the gray-scale image of the subject acquired by a projection-type image-capturing apparatus respectively, around the outline.

The image processing method may further include steps of extracting gray-scale image of a plurality of the subjects facing a plurality of angles, from a single gray-scale image acquired by the projection-type image-capturing apparatus, and generating 3-dimensional image data by distributing respectively the extracted gray-scale image, around the outline. In this case, the subject may constitute substance which has a helical symmetry, while the apparatus deals with gray-scale image of the substance as the single gray-scale image. Further to this case, the image processing method may further include steps of recognizing a reference angle, which is an angle the single subject as a reference faces, and calculating angles which each of the subjects faces by adding or subtracting from the reference angle, the angle which the helix rotates by the single subject.

The fifth aspect of the present invention provides a computer executable program for image processing for acquiring 3-dimensional data of a subject by processing image data of the subject. The program includes a shape computing unit operable to calculate shape data which represent a structural configuration of the subject, using a plurality of 1st image data of the subject obtained by projecting the subject toward the plural angles, and a first integrating unit operable to integrate the shape data and gray-scale image of the subject acquired by a projection-type image-capturing apparatus.

The sixth aspect of the present invention provides a computer executable program for image processing for acquiring 3-dimensional data of a subject by processing image data of the subject. The program includes a shape computing unit operable to calculate an outline of the subject, using a plurality of 1st image data of the subject obtained by projecting the subject toward the plural angles, and an image data generating unit operable to generate 3-dimensional image data by distributing density of the gray-scale image of the subject acquired by a projection-type image-capturing apparatus, around the outline.

The seventh aspect of the present invention provides a computer-readable medium which stores therein a program for image processing for acquiring a 3-dimensional data of a subject by processing an image data of the subject. The program includes a shape computing unit operable to calculate a shape data which represent an structural configuration of the subject, using a plurality of 1st image data of the subject obtained by projecting the subject toward the plural angles and a first integrating unit operable to integrate the shape data and a gray-scale image of the subject, acquired by a projection-type image-capturing apparatus.

The eighth aspect of the present invention provides a computer-readable medium which stores therein a program for image processing for acquiring a 3-dimensional data of a subject by processing an image data of the subject. The program includes a shape computing unit operable to calculate an outline of the subject, using a plurality of 1st image data of the subject obtained by projecting the subject toward the plural angles, and an image data generating unit operable to generate 3-dimensional image data by distributing a density of the gray-scale image of the subject, acquired by a projection-type image-capturing apparatus, around the outline.

This summary of invention does not necessarily describe all necessary features so that the invention may also be a sub-combination of these described features.

DETAILED DESCRIPTION OF THE INVENTION

The invention will now be described based on preferred embodiments, which do not intend to restrict the scope of the present invention, but rather to exemplify the invention. All of the features and the combinations thereof described in the embodiments are not necessarily essential to the invention.

The First Embodiment

Figure 1:
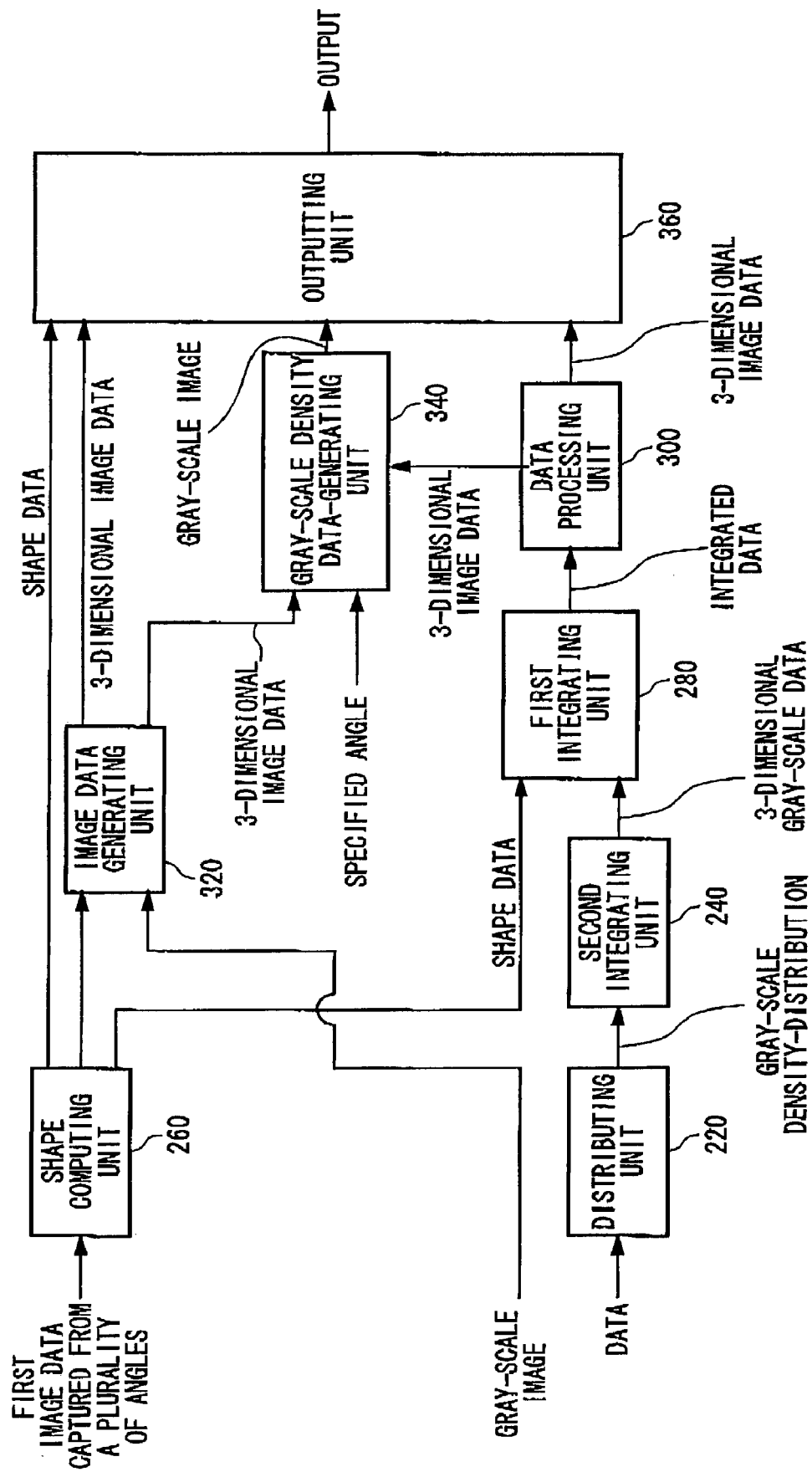
FIG. 1 shows a configuration of an image processing apparatus 200.

FIG. 1 shows a configuration of an image processing apparatus 200, which is a first embodiment of the present invention. The image processing apparatus 200 includes a distributing unit 220, a second integrating unit 240, a shape computing unit 260, a first integrating unit 280, a data processing unit 300, an image data generating unit 320, a gray-scale density data-generating unit 340, and an outputting unit 360. The image processing apparatus 200 is an apparatus which acquires 3-dimensional information regarding structural configuration of a subject using 1st image data obtained by projecting the subject toward the plural angles, and a plurality of projected image data, that is, gray-scale image acquired by the transmission electron microscope and the like. A gray-scale image can also be used as the 1st image data.

The distributing unit 220 generates gray-scale density-distributions by spreading and distributing respectively a plurality of gray-scale image acquired from external, within captured angles, that is, within projected angles, and outputs them to the second integrating unit 240. For example, the distributing unit 220 distributes densities of gray-scale image equally along the direction of spreading.

The second integrating unit 240 generates 3-dimensional gray-scale data by integrating a plurality of gray-scale density-distributions by the distributing unit 220, maintaining the angles, and outputs the information to the first integrating unit 280. The generated 3-dimensional gray-scale data corresponds to information which expresses a subject with 3-dimensional image data- False information may be included in the 3-dimensional gray-scale data here.

A shape computing unit 260 calculates height information on specific points of the subject, that is, processing objective points, from three or more image data captured from three or more angles, and calculates shape data which represent outline of the subject using the height information on a plurality of the processing objective points.

Figure 2:
FIG. 2 shows a configuration of a shape computing unit 260.

FIG. 2 shows an example of a configuration of the shape computing unit 260. The computing unit 260 includes a position relating unit 262, a height data computing unit 264, and a shape data computing unit 266.

The position relating unit 262 recognizes positions of a plurality of processing objective points in two set of the image data which is consecutive in the order of an angle, relates them respectively, and outputs them to the height data computing unit 264.

In detail, relating positions of the processing objective points in 1st image data and 2nd image data, which is consecutive in order of angles, and relating positions of the processing objective points in the 2nd image data and the 3rd image data just next to the 2nd in order of angles. This relating process is performed sequentially also to the other image combinations such as the 3rd and 4th image data, and so on. Each of the processing objective points is related in 2 or more sets of image combination, respectively.

Moreover, the position relating unit 262 defines a base line in the image data, and measures distances of the base line and the processing objective points. When a difference of the distances from the base line to the processing objective points in two images, which constitute an image combination, is more than a predetermined level, the position relating unit performs again the position recognitions and the relations to the processing base line.

Here, the position relating unit relates the positions of processing objective points using the above mentioned predetermined angle when each of the images are captured with a rotation of the subject by the predetermined angle with the same rotation axis as the rotation center, or the 1st and 2nd images among three or more image data, are captured with a rotation of the subject by a predetermined angle with a rotating axis as a rotating center, and the 3rd image are captured with a rotation of the subject with another rotating axis as a rotating center, by the predetermined angle, from the position where the 1st image was captured.

A height data computing unit 264 calculates height information of the processing objective points related by the position relating unit 262 in two set of image data respectively, and outputs them to the shape data computing unit 266. The processing performed by the height data computing unit 264 is same as the so-called processing of a stereoscopic vision method. Here, since each of the processing objective points is related in at least 2 or more sets of image combination respectively, the height data computing unit 264 calculates two or more height information of each of the processing objective points. The height data computing unit 264 calculates height information which should be outputted by the least-squares error method based on a plurality of height information. When the error by the least-squares error method is more than a predetermined value, the position relating unit 262 re-detects the positions of processing objective points.

A shape data computing unit 266 calculates shape data of the subject using height information of the processing objective points which the height data computing unit 264 calculated, and plane information of the processing objective points calculated from the image data. The shape data computing unit 266 outputs the calculated shape data to the image data generating unit 320, the first integrating unit 280, and the outputting unit 360.

Returning to FIG. 1, the first integrating unit 280 generates a integrated image by integrating shape data by the shape computing unit 260 on 3-dimensional gray-scale data by the second integrating unit 240, and outputs the image to the data processing unit 300.

The data processing unit 300 generates 3-dimensional image data by extracting only information which exists around the shape data or information which lap with the shape data, from 3-dimensional gray-scale density-distributions, using the integrated image which the first integrating unit 280 outputted, and outputs the 3-dimensional image data to the gray-scale density data-generating unit 340 and the outputting unit 360. When the false information is included in the 3-dimensional gray-scale data, there is no lapping between the false information and the shape data. Therefore, false information is not included in the information that the data processing unit 300 extracts. Consequently, the 3-dimensional image data correspond to information representing a 3-dimensional structure of the subject with more accuracy.

The image data generating unit 320 generates 3-dimensional image data of the subject by distributing the gray-scale image acquired from the external, around the corresponding part of the outline which is shown by the shape data which the shape computing unit 260 calculated, and outputs the generated 3-dimensional image data to the gray-scale density data-generating unit 340 and the outputting unit 360. For example, an image data generating unit 320 generates the 3-dimensional gray-scale image by distributing densities of the gray-scale image evenly only over the area which is in a predetermined range from the part of the outline.

Here, false information does not arise because the image data generating unit 320 generates 3-dimensional image data of the subject, without going through processes of spreading and integrating the gray-scale image, within the captured angle.

The gray-scale density data-generating unit 340 generates a projected image captured from an angle specified using the 3-dimensional image data which the image data generating unit 320 or the data processing unit 300 generated, that is, gray-scale image of the subject, and outputs the data to the outputting unit 360. A gray-scale density data-generating unit 340 acquires the specified angle through external input device, such as a keyboard.

The outputting unit 360 outputs the shape data by the shape computing unit 260, the 3-dimensional image data by the image data generating unit 320, the 3-dimensional image data by the data processing unit 300, and the gray-scale image by the gray-scale density data-generating unit 340 to an external printer or external display and the like.

Figure 3:
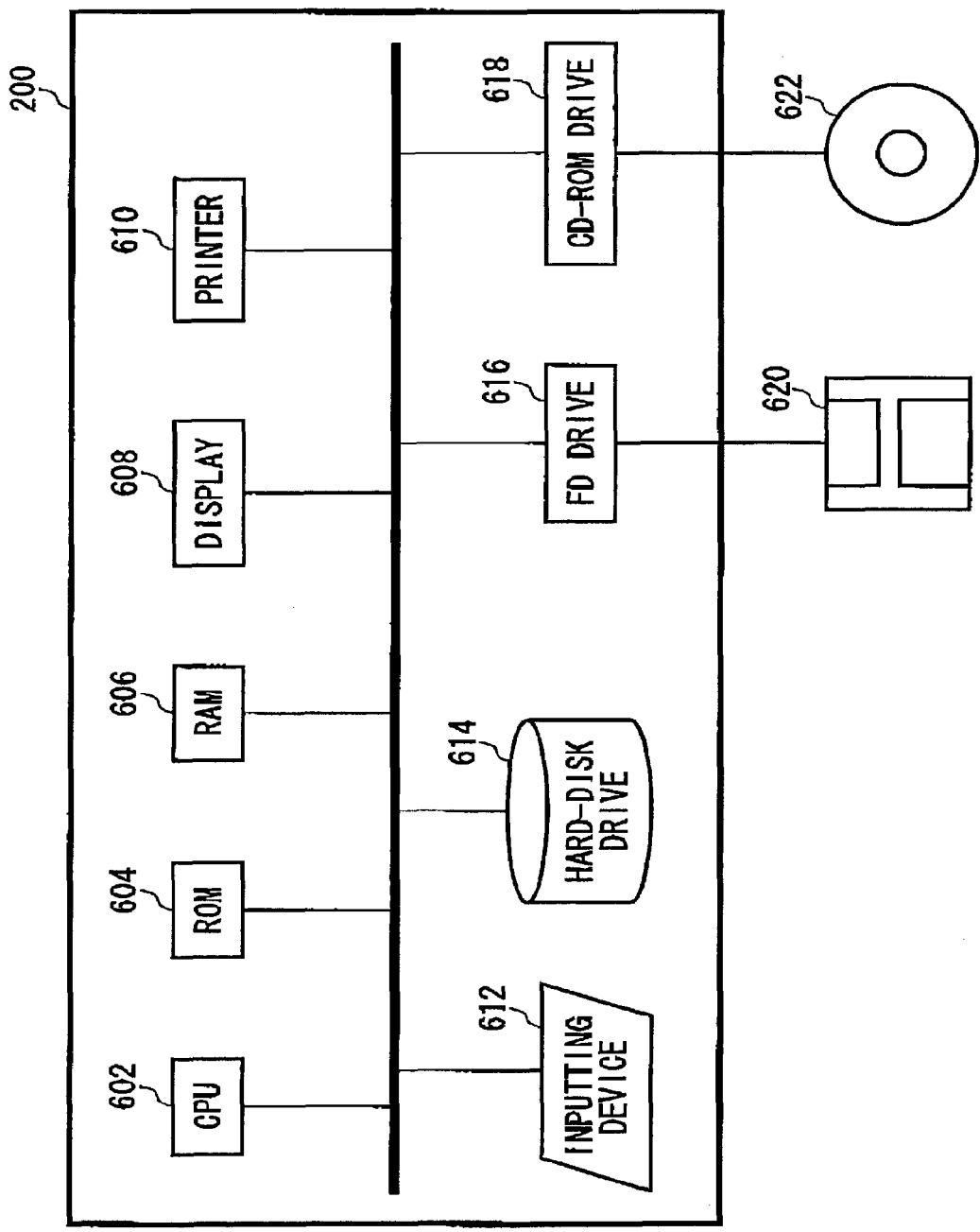
FIG. 3 shows an example of a hardware block diagram of an image processing apparatus 200.

FIG. 3 shows an example of the hardware block diagram of an image processing apparatus 200. In the present embodiment, the image processing apparatus 200 has CPU (central processing unit) 602, ROM (read only memory) 604, RAM (random access memory) 606, display 608, a printer 610, an input device 612, a hard disk drive unit 614, the FD (floppy disk) drive 616, and the CD-ROM (compact disk ROM) drive 618.

The CPU 602 performs processing based on the program stored in the RAM606 and the ROM604. The display 608 displays various information. A printer 610 prints various information. The input device 612 inputs setup and the like for the image processing apparatus 200. The FD drive 616 reads data or a program from the floppy (registered trademark) disk 620, and passes them to CPU 602. The CD-ROM drive 618 reads data or a program from the CD-ROM 622, and passes them to CPU 602. The hard disk 614 stores the data or the program read by the FD drive 616 or CD-ROM drive 618, and the data created by the CPU 602 executing a program, and passes them to CPU 602 by reading out the memorized data.

In the present embodiment, from CD-ROM 622 which has a program which realizes each functional unit of the image processing apparatus 200 mentioned above, the program concerned is read and installed to the hard disk 618 in advance, and the functional unit of the above-mentioned image processing apparatus 200 is realized by the CPU 602 reading the program concerned from the hard disk 618 and executing the program.

The program more specifically includes a distribution module for realizing a distributing unit 220, a 2nd integrating module for realizing the second integrating unit 240, a form calculation module for realizing the shape computing unit 260, a 1st integrating module for realizing the 1st integrating unit 280, a data processing module for realizing the data processing unit 300, an image data generating module for realizing the image data generating unit 320, a gray density generating module for realizing the gray-scale density data-generating unit 340, and an outputting module for realizing the outputting unit 360. Moreover, the program may be stored in the other recording media, such as the floppy disk (registered trademark) 620, magneto-optical disk (MO) and minidisk (MD), other than the CD-ROM 622.

Next, referring to FIG. 4-FIG. 11, a 1st operation example of the image processing apparatus 200 is explained. In this example, two hemispherical subjects 400 which stand in a line parallel and upward are captured with a projection-type image capturing apparatus, and 3-dimensional image data is generated by the image processing apparatus 200.

Figure 4:
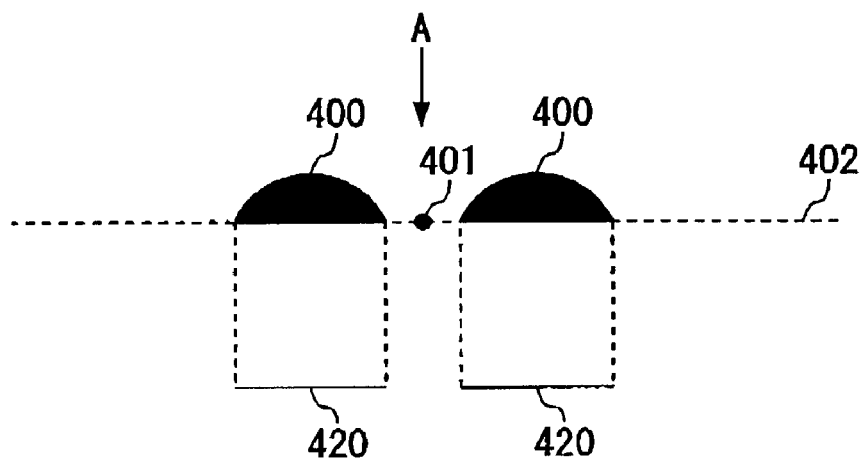
FIG. 4 is a figure explaining how to acquire gray-scale image.
Figure 5:
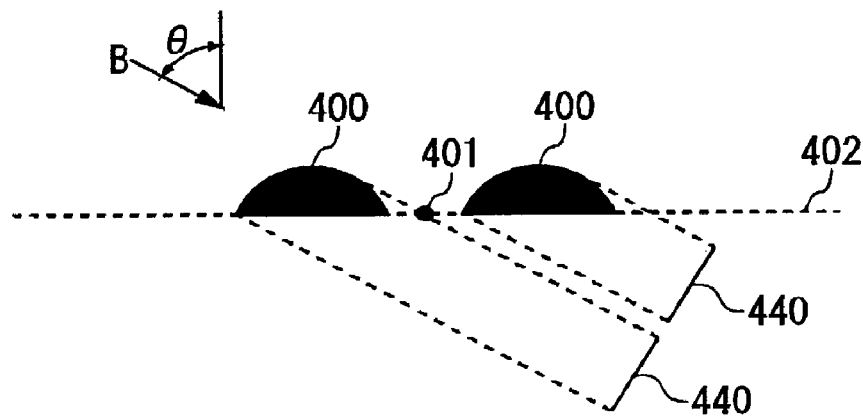
FIG. 5 is a figure explaining how to acquire gray-scale image.
Figure 6:
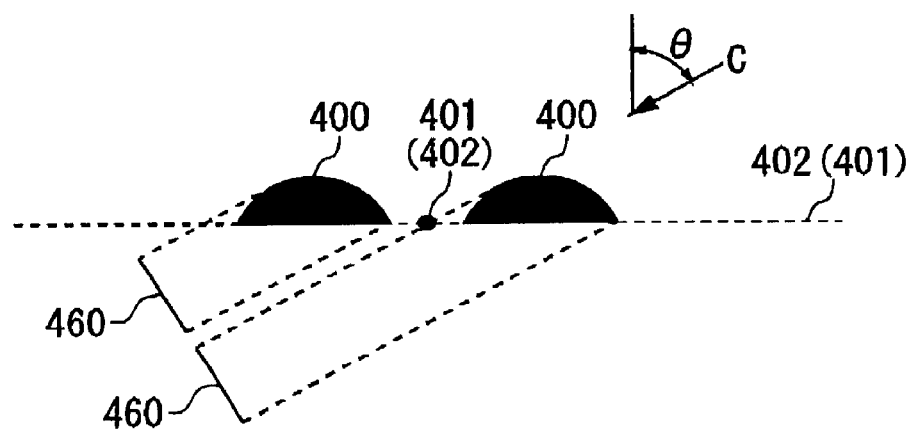
FIG. 6 is a figure explaining how to acquire gray-scale image.

First of all, a step of acquiring gray-scale image is explained. As shown in FIG. 4, FIG. 5, and FIG. 6, a subject is captured from at least three different angles (in this example, the direction of A, the direction B, and the direction C), and projected image data, that is, gray-scale image 420, 440, and 460, are acquired. Here, it is desirable to make the angle interval of the direction A and the direction B, and the angle interval of the direction A and the direction C into the equal value "theta" respectively, as shown in FIG. 4, FIG. 5 and FIG. 6.

Moreover, the direction B, and the direction C may be directed at the angle rotated from the direction A with a same axis 401 as the rotation center, or may be directed at the angle rotated respectively from the direction A with different axes 401 and 402 as rotation centers.

Then, the gray-scale image 420, 440, and 460 are inputted into the image processing apparatus 200. The gray-scale image 420, 440, and 460 functions also as the 1st image data here.

In this example, the distributing unit 220 of the image processing apparatus 200 generates gray-scale density-distributions 425, 445, and 465, by spreading each of the gray-scale image 420, 440, and 460 along the image-capturing direction, and the second integrating unit integrates gray-scale density-distributions 425, 445, and 465, keeping each angle, and generates 3-dimensional gray-scale data.

Figure 7:
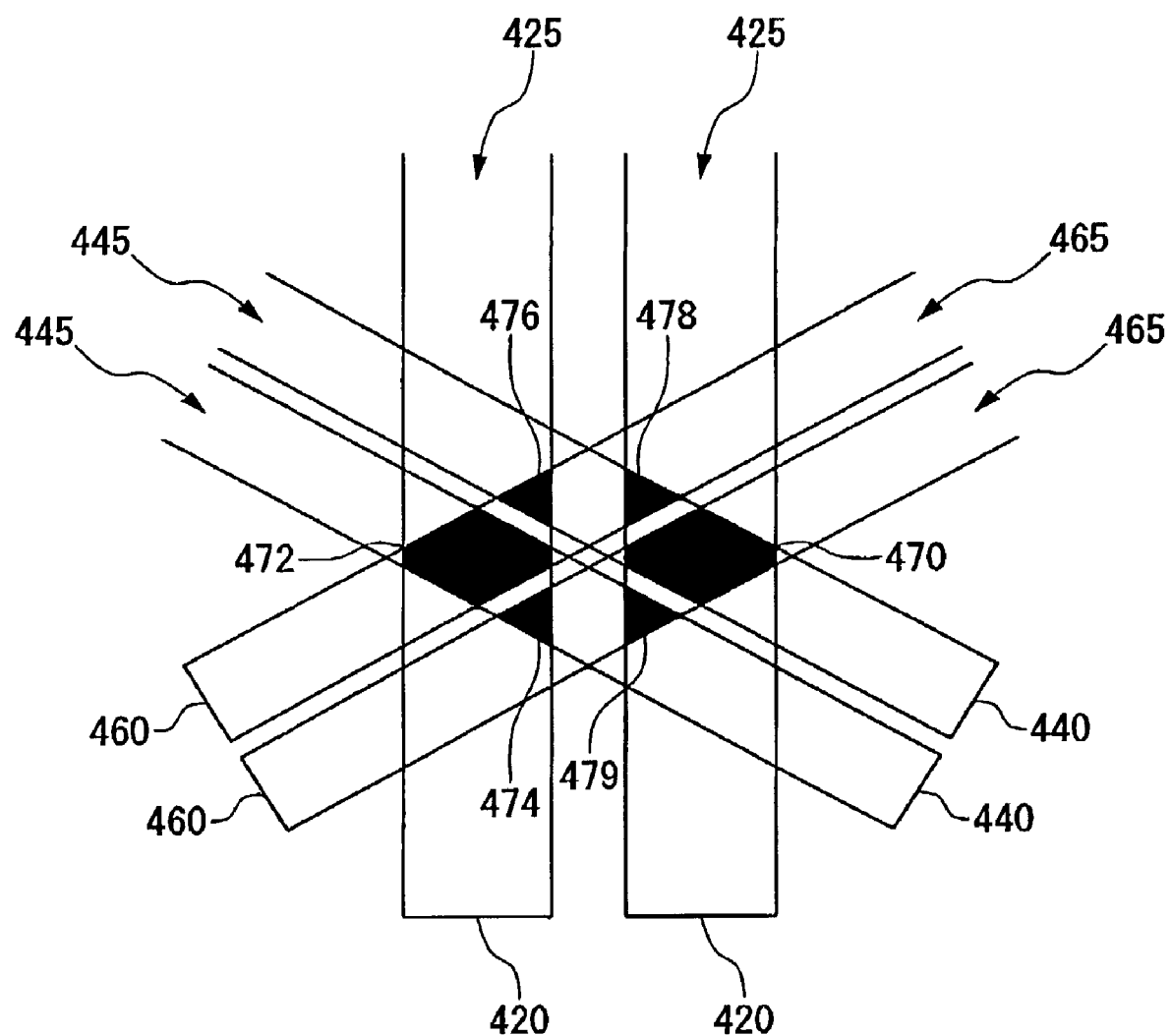
FIG. 7 shows longitudinal-section information on an example of 3-dimensional gray-scale data.

FIG. 7 shows an example of longitudinal-section information of the 3-dimensional gray-scale data in the present embodiment. The 3-dimensional gray-scaled at a show that object exists at the position where all of the gray-scale density-distributions lap. FIG. 7 shows that a subject 400 exists where all of the gray-scale density-distributions 425, 445, and 465 lap, that is, the part 470, 472, 474, 476, 478, and 479. However, because the number of subject 400 originally is two, four of the above six information are false information.

Figure 8:
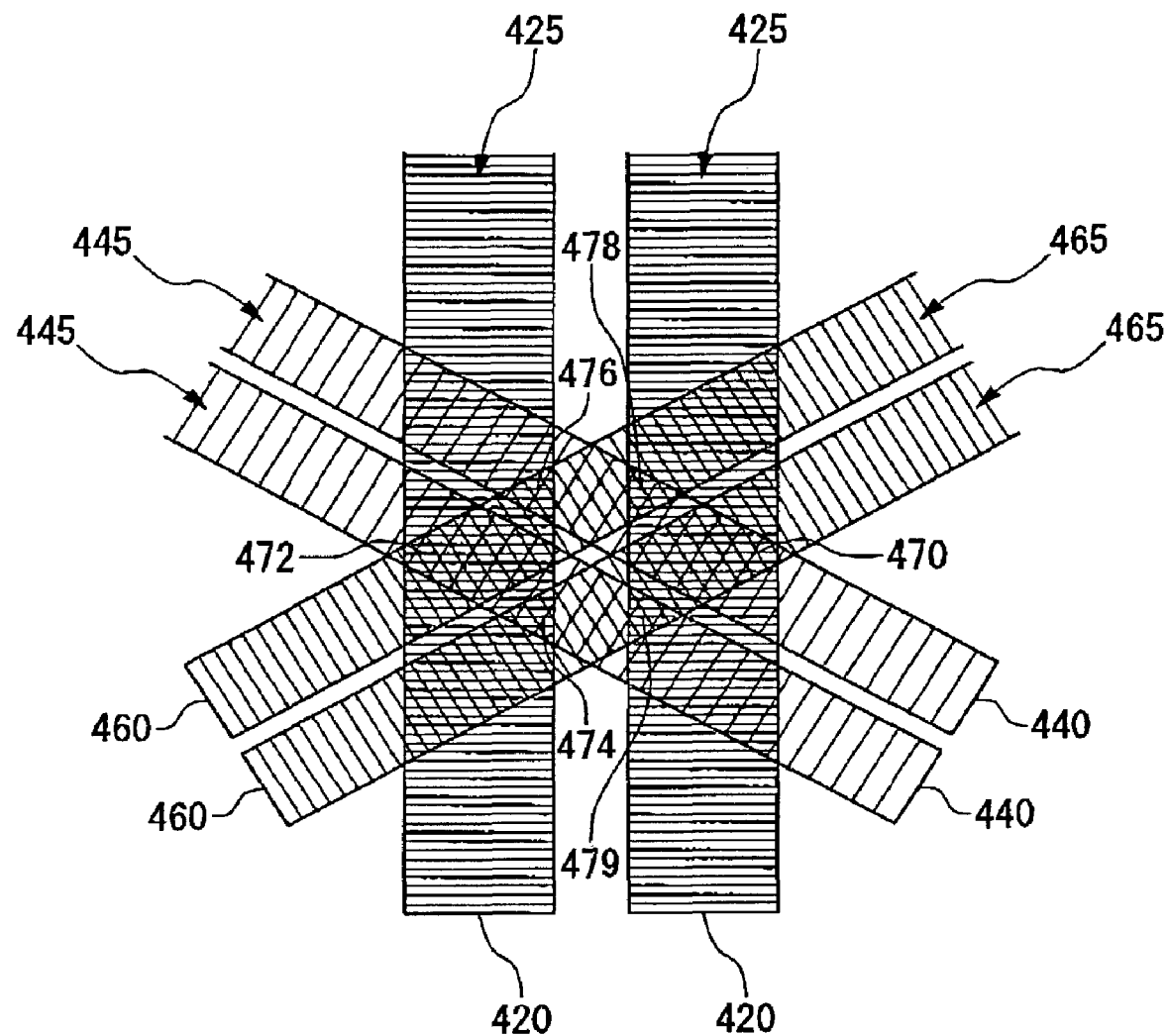
FIG. 8 shows another example of the longitudinal-section information on the 3-dimensional gray-scale data.

FIG. 8 shows another example of the longitudinal-section information on the 3-dimensional gray-scale data in the present embodiment. In the present embodiment, densities of gray-scale image 420, 440, and 460 differs, respectively. Moreover, gray-scale density-distributions 425, 445, and 465 are obtained by spreading the densities of the gray-scale image 420, 440, and 460 within the captured angles, and distributing the densities evenly. In this case, since positions other than data 470-479 may also have more than equivalent densities to one of the data 470-479, the false information may increase further.

Moreover, the shape computing unit 260 of the image processing apparatus 200 calculates the shape data 265 which represent an outline of the subject 400 from the gray-scale image 420, 440, and 460. The shape computing unit 260 can not calculate whole outline of the subject 400, but calculate the position commonly included in the range of vision of the direction A, the direction B, and the direction C in the figure. In this example, an outline of only a spherical part of the subject 400 is calculated.

And the first integrating unit 280 of the image processing apparatus 200 superimposes the shape data by the shape computing unit 260 on the 3-dimensional gray-scale image.

Figure 9:
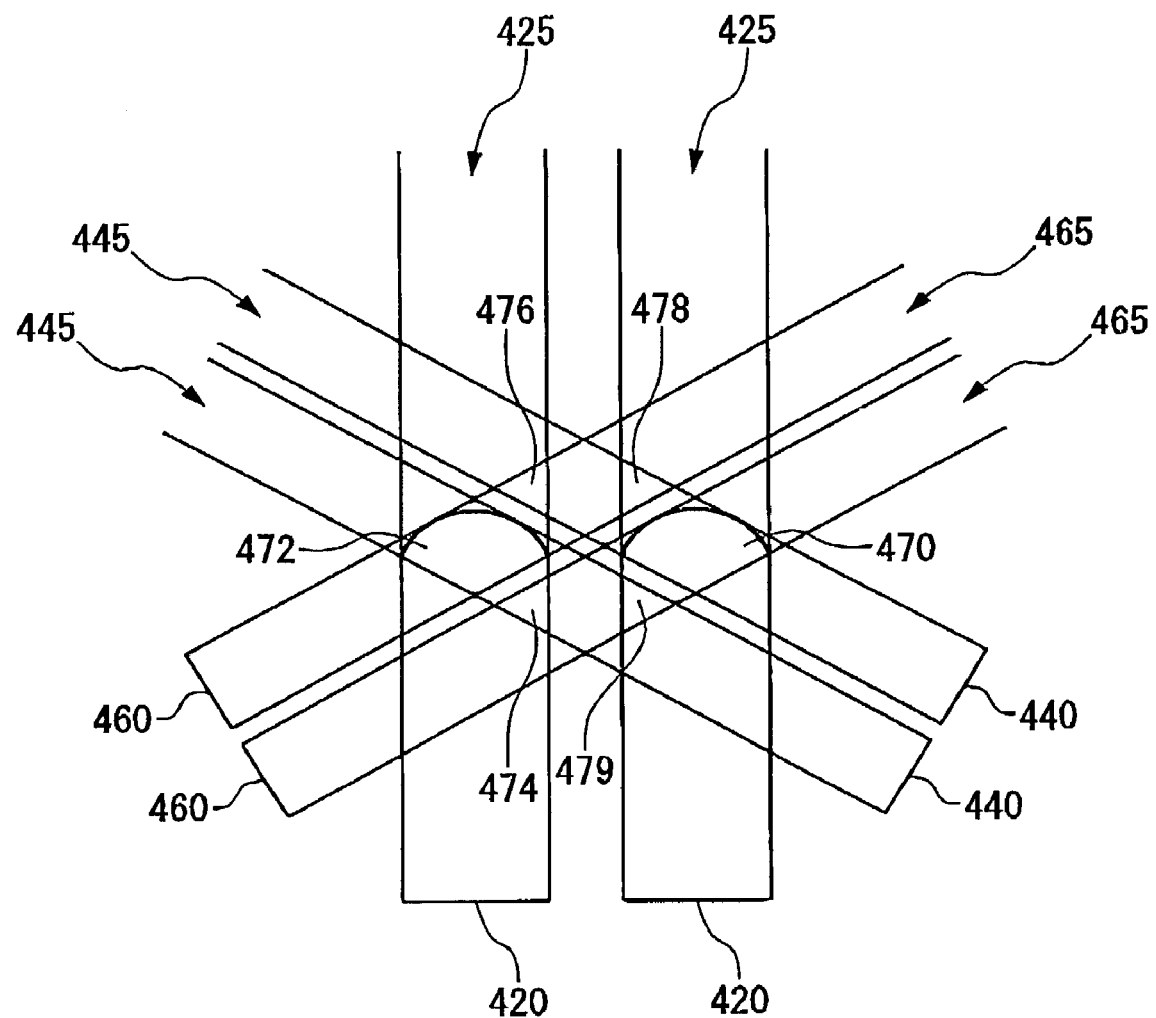
FIG. 9 shows the longitudinal-section information on an example of a integrated image by a first integrating unit 280.

FIG. 9 shows longitudinal-section information on the integrated image by the first integrating unit 280 in the present embodiment. In the present embodiment, two shape data 265 by the shape computing unit 260 lap with data 470 and 472 respectively. Therefore, the data processing unit 300 judges that the data 470 and 472 are true data that express the object, and the data 474, 476, 478, and 479 are false data, then extracts only the data 470 and 472, and outputs them to the gray-scale density data-generating unit 340 and the outputting unit 360 as 3-dimensional image data.

Consequently, the false data never be included in the 3-dimensional image data.

Here, when the reliability of the shape data 265 is high, the data processing unit 300 outputs the 3-dimensional image data which considered the shape data 265. Moreover, when the gray-scale density-distributions 425, 445, and 465 are not in focus, the boundary of the data 470 and the boundary of 472 do not become clear. In this case, the data processing unit 300 considers the data which exist within a distance defined in advance from the shape data 265, as the data 470 and 472.

Moreover, human operation may substitute for the operation of the data processing unit 300, and the false data may be removed by involving a judgment of the human into the 3-dimensional image data by the data processing unit 300, displaying a integrated data by the first integrating unit 280 on a display and the like. In this case, the false data can be removed corresponding to cases more properly.

Figure 10:
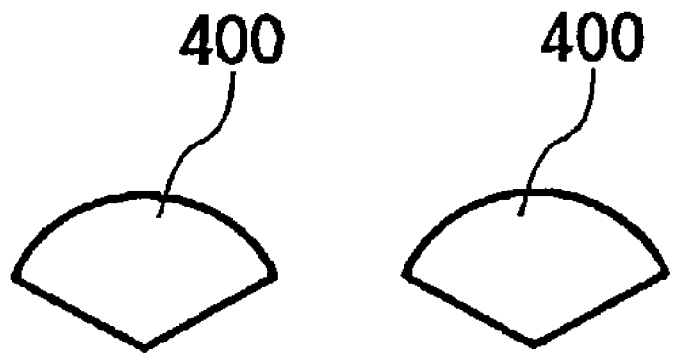
FIG. 10 shows the longitudinal section of an example of the 3-dimensional image data by a data processing unit 300.

FIG. 10 shows longitudinal section of the 3-dimensional image data by the data processing unit 300 in the present embodiment. It shows that the 3-dimensional image data by the data processing unit 300 are recreating the subject 400 with sufficient accuracy.

Figure 11:
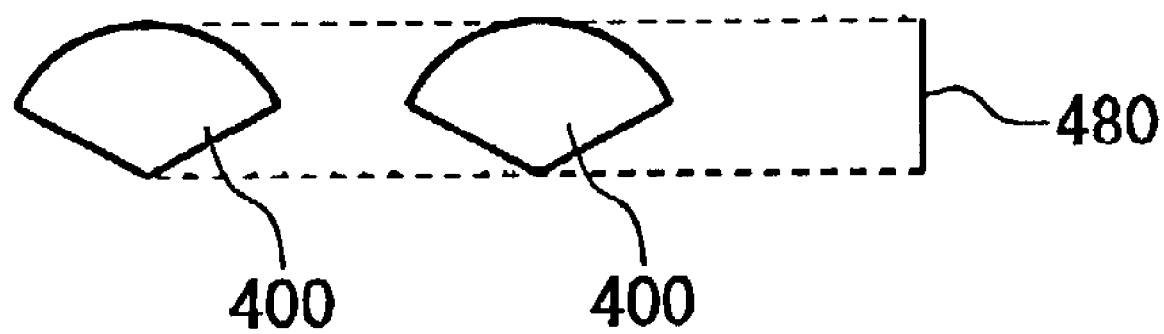
FIG. 11 shows an example of operation by a gray-scale density data-generating unit 340.

FIG. 11 shows an example of operation of the gray-scale density data-generating unit 340. In this example, the gray-scale density data-generating unit 340 generates projected image, that is, gray-scale image 480, captured from just beside in the figure, that is, from a different angle from the gray-scale image 420, 440, and 460 inputted with the 3-dimensional data by the data processing unit 300. As shown in FIG. 11, the gray-scale density data-generating unit 340 can generate the projected image captured from any specified angles, that is, the gray-scale image, and output it to the outputting unit 360.

Here, in the example of FIG. 11, the gray-scale image 480 which the gray-scale density data-generating unit 340 generated is not exactly same as the gray-scale image which is obtained by seeing the subject 400 from just beside. This is because the 3-dimensional image data by the data processing unit 300 does not match the subject 400 exactly.

However, when the gray-scale image inputted into the image processing apparatus 200 is the image by a transmission electron microscope, gray-scale image includes gradation even within an atom or a molecule. The 3-dimensional image data calculated become more closer to the subject 400 by the second integrating unit 240 integrating the gray-scale image from further more angles, and the data processing unit 300 deleting a position where the density is low in consideration of the gradation described above. Consequently, the gray-scale image which the gray-scale density data-generating unit 340 generates becomes still closer to the gray-scale image acquired by actual image.

And the outputting unit 360 outputs the shape data 265 by the shape computing unit 260, the 3-dimensional image data by the data processing unit 300, that is, data 470, and data 472, and the gray-scale image by the gray-scale density data-generating unit 340 to a display or a printer as required.

Thus, in the first example of the operation, the image processing apparatus 200 acquires more exact 3-dimensional image data using the distributing unit 220, the second integrating unit 240, the shape computing unit 260, the first integrating unit 280, and the data processing unit 300.

Figure 12:
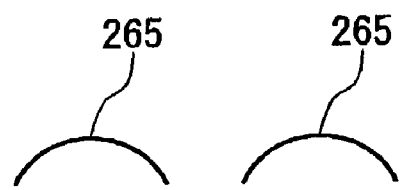
FIG. 12 is a figure for explaining a second example of operation by an image processing apparatus 200.
Figure 13:
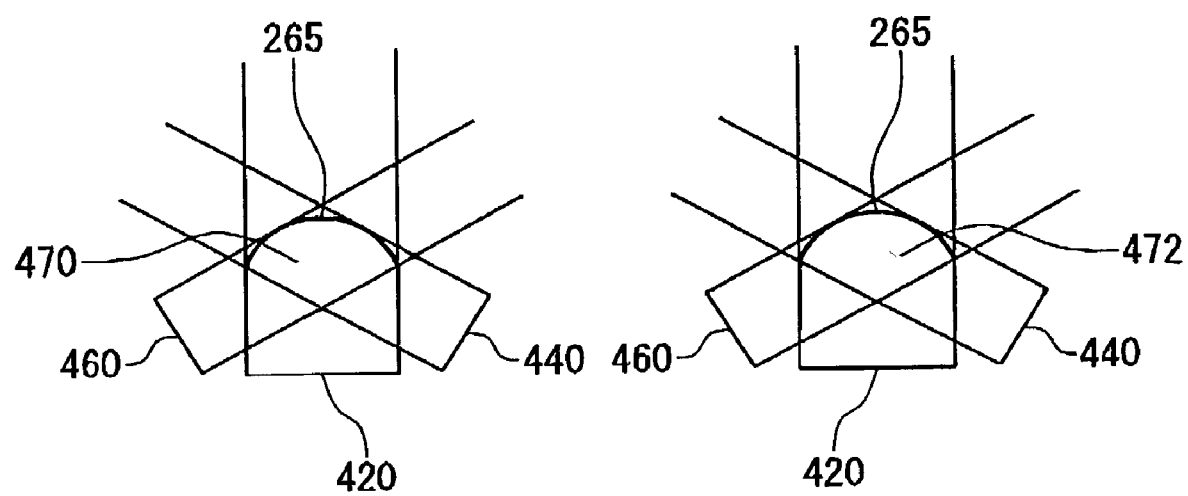
FIG. 13 is a figure for explaining a second example of operation by an image processing apparatus 200

Next, with reference to FIG. 12 and 13, the second example of operation of the image processing apparatus 200 is explained. In this example, the image processing apparatus 200 acquires 3-dimensional image data of the subject 400 using gray-scale image 420, 440, and 460 in the same way as the first example of operation.

First, the shape computing unit 260 calculates shape data 265 as illustrated in FIG. 12. Then, the image data generating unit 320 distributes the gray-scale image 420, 440, and 460 only over the perimeter of the shape data 265, as illustrated in FIG. 13, and considers parts where all of the three gray-scale image lap, that is, the data 470 and 472, as the 3-dimensional image data. Consequently, the false data never be included in the 3-dimensional image data.

Here, when the reliability of the shape data 265 is high, the image data generating unit 320 outputs 3-dimensional image data which considered the shape data 265. Moreover, when a boundary of the data 470, and a boundary of the data 472 are not in focus, the image data generating unit 320 considers data that exist within a distance defined in advance from the shape data 265, as the data 470 and 472. Here, when the reliability of the shape data 265 is high, the image data generating unit 320 outputs the 3-dimensional image data which considered the shape data 265. Moreover, when the gray-scale density-distributions 425, 445, and 465 are not in focus, the boundary of the data 470 and the boundary of 472 do not become clear. In this case, the image data generating unit 320 considers data that exist within a distance defined in advance from the shape data 265, as the data 470 and 472. For example, when thickness D of the subject 400 is known, densities of the gray-scale image 420, 440, and 460 are distributed evenly within a range of the thickness D from the outline. In this case, it is still more preferable for the above-mentioned densities, to be distributed along the projection direction only within the range of thickness D.

Then, the gray-scale density data-generating unit 340 generates a projected image captured from a different angle from the gray-scale image 420, 440, and 460 inputted with the 3-dimensional data by the image data generating unit 320, that is, gray-scale image.

Thus, in the second example of operation, the image processing apparatus 200 acquires more exact 3-dimensional image data with the shape computing unit 260 and the image data generating unit 320.

As mentioned above, according to the image processing apparatus 200, 3-dimensional image data that express a structural configuration of a subject with more accuracy can be acquired by using the projected image data obtained by projecting the subject toward the plural angles.

The image processing apparatus 200 demonstrates the above-mentioned merit especially when the range of angle, in which the image processing apparatus 200 can capture an image, is limited. For example, when dealing with the image data acquired by a transmission electron microscope as the projected image data, the angle, in which the microscope can capture an image, is limited. However, it becomes possible to clarify a structural configuration of a subject to a molecule level by using the image processing apparatus 200.

As a detailed example, there is a case where it is desirable to clarify a structure of a protein of cells and to clarify changes thereof. In this case, the 3-dimensional data which represent the structural configuration of a protein, which is considered to be the subject, can be acquired where false data, that is, so-called ghost are removed, by capturing images of a pattern of the protein obtained by so-called quick-freezing deep-etch replica method by the transmission electron microscope, and processing the images with the image processing apparatus 200.

The Second Embodiment

Figure 14:
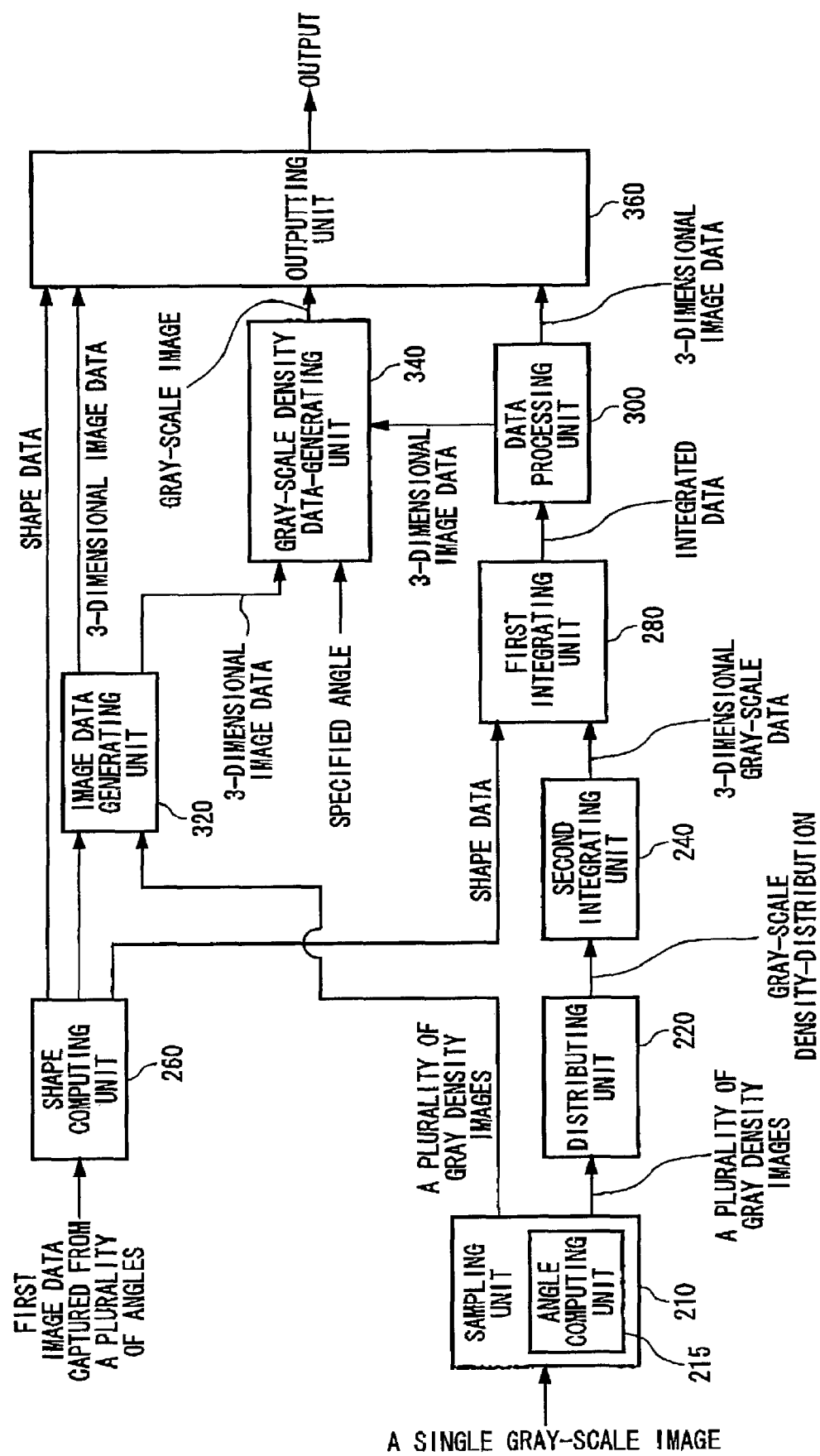
FIG. 14 shows a configuration of an image processing apparatus 201 which is a second embodiment of the present invention.

FIG. 14 shows a configuration of an image processing apparatus 201, which is a second embodiment of the present invention. The image processing apparatus 201 includes, as functional units, a sampling unit 210, the distributing unit 220, the second integrating unit 240, the shape computing unit 260, the first integrating unit 280, the data processing unit 300, the image data generating unit 320, the gray-scale density data-generating unit 340, and the outputting unit 360. A sampling unit 210 further includes an angle computing unit 215.

Figure 15:
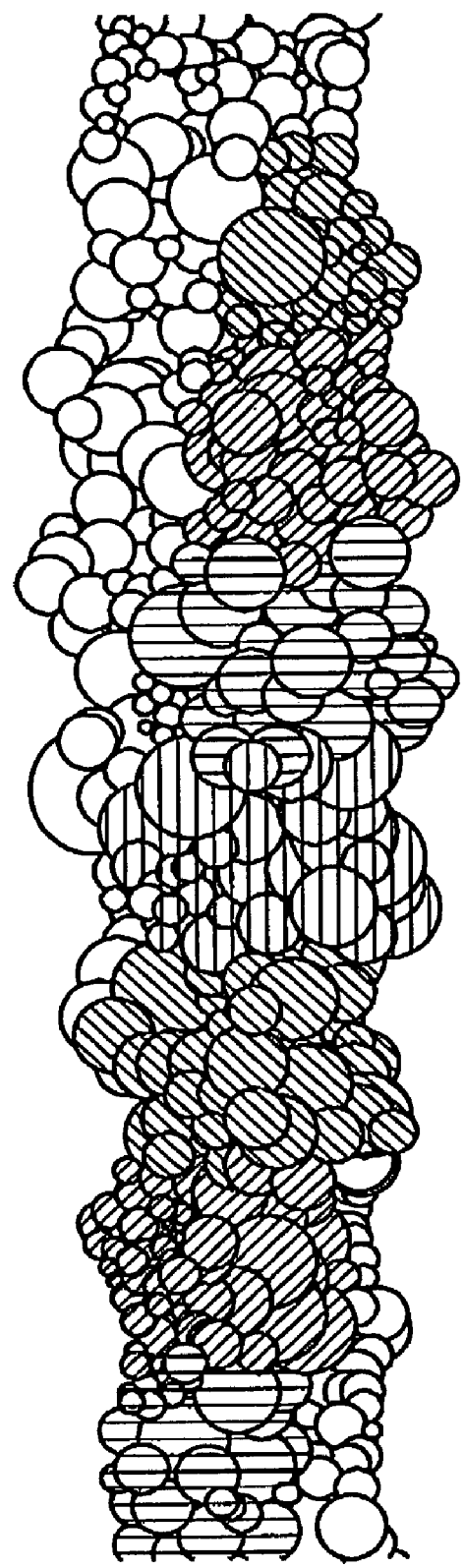
FIG. 15 shows a particle 491, which is an example of the subject constituting the substance 490, which has a helical symmetry.

The image processing apparatus 201 is an apparatus which extracts gray-scale image of a plurality of subjects facing along a plurality of angles respectively, included in a single gray-scale image obtained by a projection-type image capturing apparatus such as an electron microscope and the like, and acquires 3-dimensional data regarding a structural configuration of the subject using a plurality of the extracted gray-scale image. Here, the subject is, as shown in FIG. 15 for example, a particle 491, which constitutes substance 490, which has a helical symmetry, such as a molecule which exists widely in a living world.

In the image processing apparatus 201, since operation of functional units other than the sampling unit 210 and angle computing unit 215 is same as the operation of the image processing apparatus 200, which is the first embodiment, the explanation thereof is omitted.

When a single gray-scale image is inputted, the sampling unit 210 extracts gray-scale image of a subject from the single gray-scale image, and outputs the image data to the distributing unit 220 and the image data generating unit 320. Here, when the above-mentioned single gray-scale image includes gray-scale image of a plurality of subjects, the sampling unit 210 extracts the gray-scale image of a plurality of the subjects respectively. Moreover, when the 1st image data is the gray-scale image, the sampling unit 210 outputs the extracted gray-scale image also to the shape computing unit 260.

The angle computing unit 215 calculates, a direction of the subject, that is, the angle, which the gray-scale image that the sampling unit 210 extracted indicates, and outputs the direction, with gray-scale image of the subject, to the distributing unit 220 and the image data generating unit 320, and depending on cases, to the shape computing unit 260.

Figure 16:
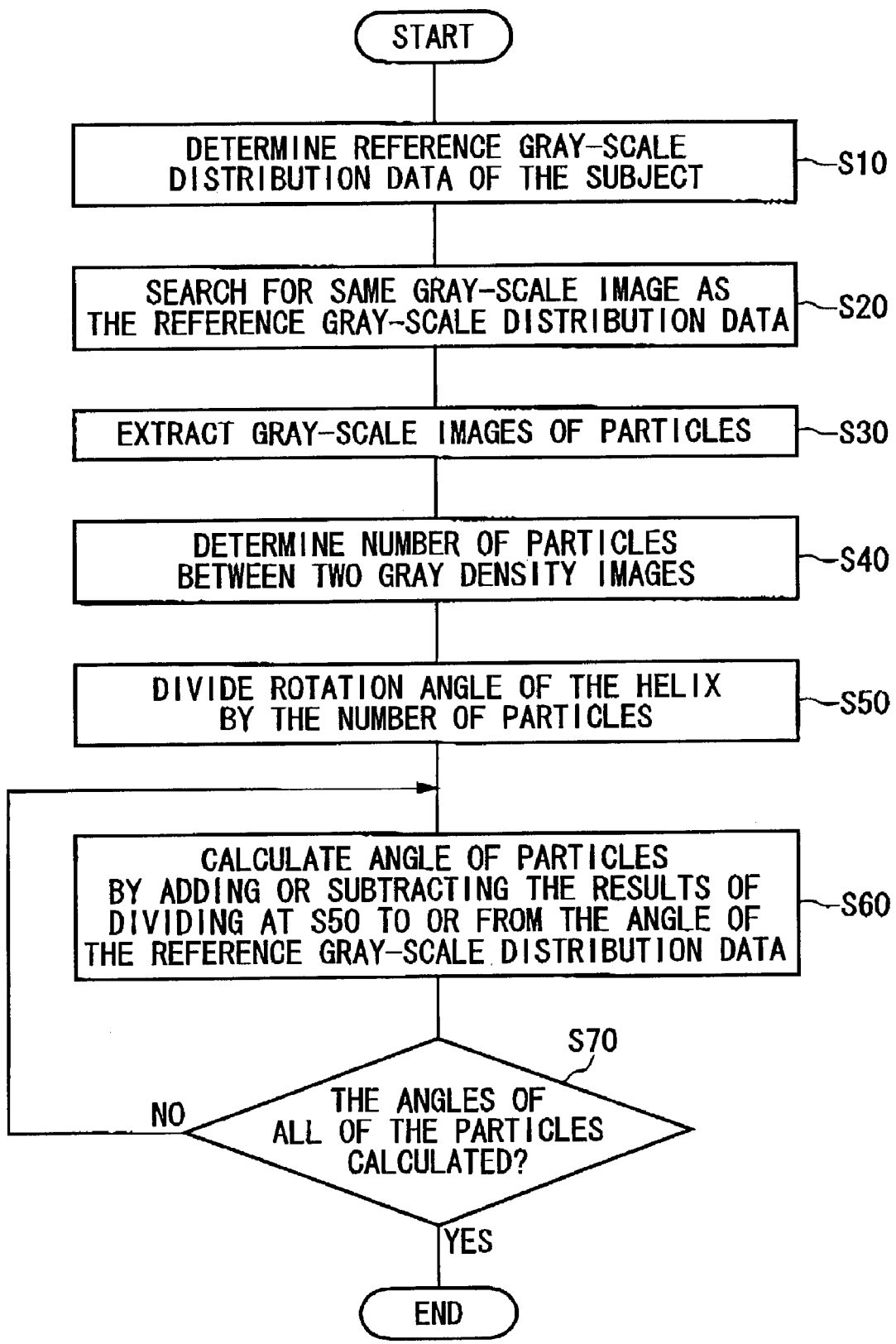
FIG. 16 shows an example of operation by a sampling unit 210 and an angle computing unit 215.

FIG. 16 shows an example of operation of the sampling unit 210 and the angle computing unit 215. This example is the case where the single gray-scale image is of the substance which has a helical symmetry, and besides, the subject is a particle which constitutes the substance with this helical symmetry.

First, the sampling unit 210 determines reference gray-scale distribution data of a subject which is treated as a reference, by external input or by itself in the above described single gray-scale image (S10). Then, searches the same gray-scale image as the reference gray-scale distribution data from the single gray-scale image described above (S20). Here, the sampling unit 210 may consider gray-scale image within a predetermined error the same gray-scale image.

And the sampling unit 210 extracts gray-scale images of a plurality of particles respectively which exist between the reference gray-scale distribution data and the gray-scale image searched in S20 (S30), Here, as a method of recognizing the gray-scale image of a particle, for example, there is a way of obtaining a distance of the gray-scale image and the reference gray-scale distribution data, and dividing the above described single gray-scale image for by each of the distance.

Then, the angle computing unit 215 recognizes the number of the gray-scale images which exist between the gray-scale image searched in S20 and the reference gray-scale distribution data, that is, the number of particles (S40), and calculates an angle by which the helix rotates by one particle by dividing a rotation angle of the helix, for example, 360 degrees, by the number of the particles recognized (S50).

Then, the angle computing unit 215 calculates angles which the particles face by adding or subtracting the angle calculated by S50 to the angle which the reference gray-scale distribution data represent (S60). Operation of S60 is repeated until the angles of all particles are calculated (S70).

Figure 17:
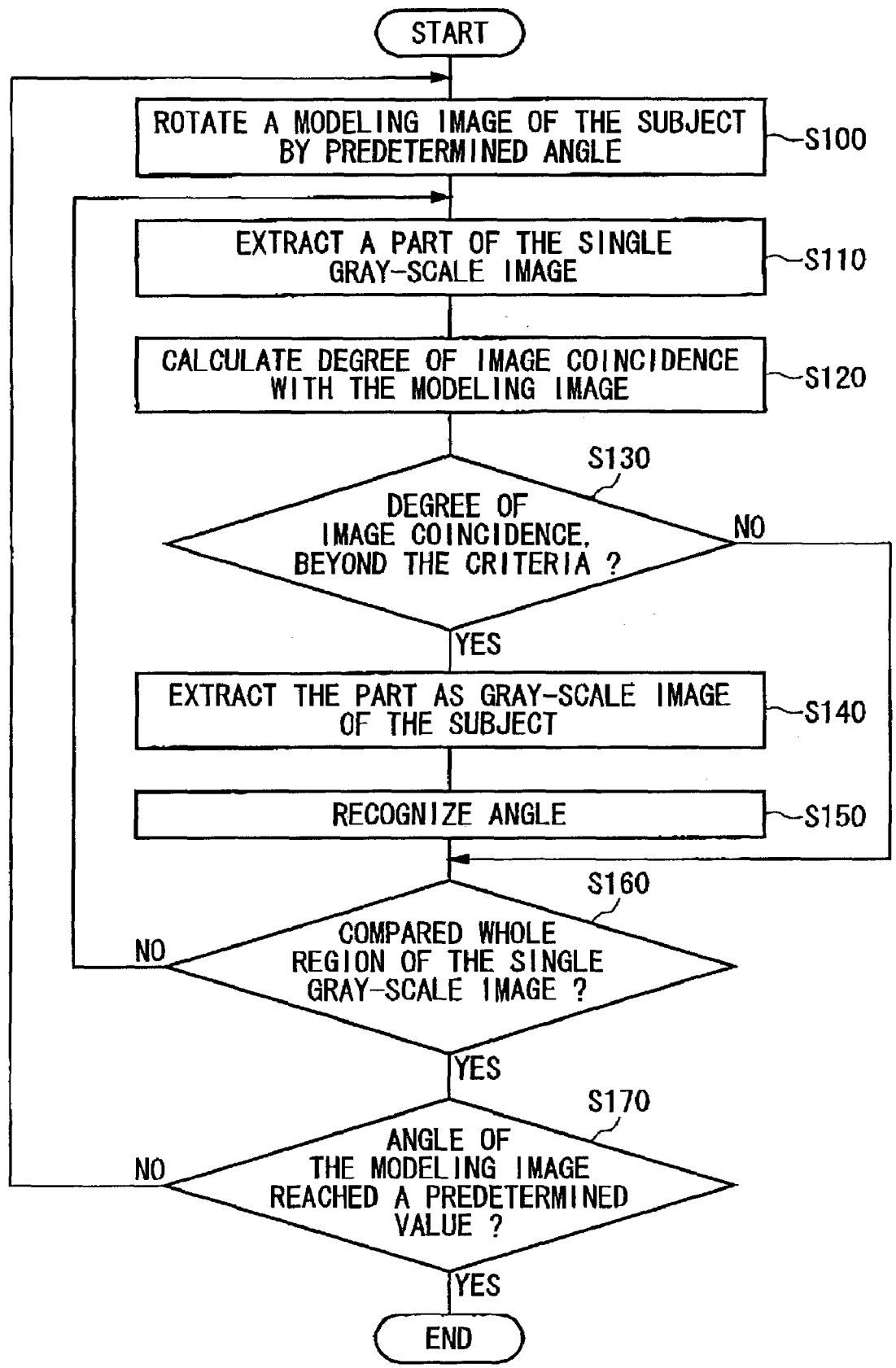
FIG. 17 shows other examples of operation by a sampling unit 210 and an angle computing unit 215.

FIG. 17 shows another example of operation by the sampling unit 210 and the angle computing unit 215. First, the sampling unit 210 rotates a modeling image of the subject by predetermined angle (S100). And the sampling unit 210 extracts a part of the above mentioned single gray-scale image (S110), and calculates the degree of image coincidence as compared with the modeling image (S120). When it is judged that the degree of the image coincidence is beyond a criteria (S130), a sampling unit 210 extracts the part concerned, recognizing it to be the gray-scale image of the subject (S140). The angle computing unit 215 recognizes the angle of rotation by S100 as the angle which the subject faces (S150).

After repeating operations from S110 to S150 over the whole region of the above mentioned single gray-scale image (S160), the sampling unit 210 and the angle computing unit 215 repeat operations from S100 to S160 until the angle reaches a predetermined angle (S170).

Thus, according to the image processing apparatus 201, since the sampling unit 210 and the angle computing unit 215 extract gray-scale image of a plurality of subjects facing different angles, from a single gray-scale image, a plurality of gray-scale image are not necessarily indispensable.

Therefore, when two or more images of substance, which has a helical symmetry, are captured, according to the image processing apparatus 201, it becomes possible to acquire clearer 3-dimensional image data by using only the clearest gray-scale image. Moreover, even when an image-capturing angle is limited due to physical restrictions of sample creation or an experimental apparatus, it becomes possible to acquire 3-dimensional image data.

Although the present invention has been described by way of exemplary embodiments, it should be understood that many changes and substitutions may be made by those skilled in the art without departing from the spirit and the scope of the present invention which is defined only by the appended claims.

It is obvious from foregoing explanation that the present invention can provide an image processing apparatus, an image processing method, a computer readable medium, and a computer program thereof, for acquiring 3-dimensional image data that correctly express a structural configuration of the subject by processing the projected image data obtained by projecting the subject toward the plural angles.

What is claimed is:

1. An image processing apparatus for acquiring 3-dimensional data regarding a structural configuration of a subject by processing image data of the subject, comprising:
   a shape computing unit which calculates shape data which represent an outline of the subject, using projected image data of the subject acquired from a plurality of angles by a transmission electron microscope;
   a first integrating unit which integrates projected image data of the subject acquired by a transmission electron microscope, on said shape data;
   a distributing unit which generates gray-scale density-distributions by stretching and distributing densities shown in said projected image data respectively within angles along which said projected image data are captured;
   a second integrating unit which generates 3-dimensional gray-scale data, which express the subject with 3-dimensional image data, by integrating a plurality of said gray-scale density-distributions generated from a plurality of said projected image data captured from a plurality of angles, wherein said first integrating unit integrates said 3-dimensional gray-scale data by said second integrating unit on said shape data; and
   a data processing unit which generates 3-dimensional image data by extracting only density which exists in perimeter of a shape that said shape data represent, from said 3-dimensional gray-scale data.

2. The image processing apparatus as claimed in claim 1, wherein image data of the pattern of said subject are used as said projected image data.

3. The image processing apparatus as claimed in claim 1, further comprising:
   a sampling unit which extracts respectively projected image data of a plurality of said subjects facing a plurality of angles, included in a single projected image data acquired by the transmission electron microscope, wherein said first integrating unit uses a plurality of said projected image data which said sampling unit extracted.

4. The image processing apparatus as claimed in claim 3, wherein said subject constitutes substance which has a helical symmetry, said apparatus dealing with projected image data of said substance as said single projected image data, further comprising:
   an angle computing unit which acquires a reference angle, which is an angle the single subject as a reference faces, and further calculates angles which each of said subjects faces by adding or subtracting the angle which the helix rotates by said single subject to or from said reference angle.

5. The image processing apparatus as claimed in claim 1, wherein said shape computing unit includes:
   a position relating unit which relates positions of processing objective points in said subject in a 1st image and a 2nd image which are consecutive in the order of angle, and relates the positions of the processing objective points in said 2nd image and a 3rd image;
   a height data computing unit which calculates height data for representing height of the position of said processing objective point using 2 sets of position relation by said position relating unit; and
   a shape data computing unit which generates said shape data of said subject using said height data of a plurality of processing objective points calculated by said height data computing unit, wherein said apparatus calculates said shape data using three or more said 1st images.

6. The image processing apparatus as claimed in claim 5, wherein said 1st image, said 2nd image, and said 3rd image are images captured with a rotation of said subject by a predetermined angle with a same rotation axis as the rotation center, and said height data computing unit calculates said height data using said predetermined angle.

7. The image processing apparatus as claimed in claim 5, wherein said 1st image and said 2nd image are images captured with a rotation of said subject by a predetermined angle with a first rotation axis as the rotation center, and said 3rd image is an image captured with a rotation of said subject by said predetermined angle from the position where said 1st image is captured with another rotation axis as the rotation center, and said height data computing unit calculates said height data using said predetermined angle.

8. The image processing apparatus as claimed in claim 5, wherein said position relating unit calculates distances in said 1st, 2nd, and 3rd images from a base line defined beforehand in said subject to said processing objective points, and re-detects positions of said processing objective points in said 1st and 2nd image, when the difference of said distance in said 1st image and said distance in said 2nd image is more than a predetermined value, and relates said processing objective points in said 2nd image and 3rd image again when the difference of said distance in said 2nd image and said distance in said 3rd image is more than a predetermined value.

9. The image processing apparatus as claimed in claim 5, wherein said height data computing unit calculates said height data by a least-squares error method with height data of said 1st and 2nd image and height data of said 2nd and 3rd image.

10. The image processing apparatus as claimed in claim 9, wherein said position relating unit re-detects the positions of said processing objective points, when an error by said least-squares error method is more than a predetermined value.

11. An image processing method utilized by a processor for acquiring 3-dimensional data of a subject by processing image data of the subject, comprising steps of:

calculating shape data which represent an outline of the subject, using projected image data of the subject acquired from a plurality of angles by a transmission electron microscope;

generating gray-scale density-distributions by stretching and distributing densities shown in projected image data of the subject acquired by a transmission electron microscope, respectively within angles along which said projected image data is captured;

generating 3-dimensional gray-scale data, which expresses the subject with 3-dimensional image data, by integrating a plurality of said gray-scale density-distributions generated from a plurality of said projected image data captured from a plurality of angles;

integrating said 3-dimensional gray-scale data on said shape data; and generating 3-dimensional image data by extracting only density which exists in perimeter of an outline that said shape data represent, from said 3-dimensional gray-scale data.

12. The image processing method as claimed in claim 11, further comprising steps of:

extracting projected image data of a plurality of said subjects facing a plurality of angles from a single projected image data acquired by the transmission electron microscope; and generating said gray-scale density-distributions using said extracted projected image data.

13. The image processing method as claimed in claim 12, wherein said subject constitutes substance which has a helical symmetry, while said apparatus deals with projected image data of said substance as said single projected image data.

14. The image processing method as claimed in claim 13, further comprising steps of:

recognizing a reference angle, which is an angle the single subject as a reference faces; and calculating angles which each of said subjects faces by adding or subtracting the angle which the helix rotates by said single subject to or from said reference angle.

15. A computer-readable medium which stores therein a program for image processing for acquiring 3-dimensional data of a subject by processing image data of the subject, said program comprising:

a shape computing unit operable to calculate shape data which represent a structural configuration of the subject, using projected image data of the subject acquired from a plurality of angles by a transmission electron microscope;

a first integrating unit operable to integrate projected image data of the subject acquired by the transmission electron microscope, on said shape data;

a distributing unit which generates gray-scale density-distributions by stretching and distributing densities shown in said projected image data respectively within angles along which said projected image data is captured;

a second integrating unit which generates 3-dimensional gray-scale data, which express the subject with 3-dimensional image data, by integrating a plurality of said gray-scale density-distributions generated from a plurality of said projected image data captured from a plurality of angles, wherein said first integrating unit integrates said 3-dimensional gray-scale data by said second integrating unit on said shape data; and a data processing unit which generates 3-dimensional image data by extracting only density which exists in perimeter of a shape that said shape data represent, from said 3-dimensional gray-scale data.

16. A computer-readable medium which stores therein a program for image processing for acquiring 3-dimensional data of a subject by processing image data of the subject, said program comprising:

a shape computing unit operable to calculate an outline of the subject, using projected image data of the subject acquired from a plurality of angles by a transmission electron microscope; and an image data generating unit operable to generate 3-dimensional image data by distributing density of the projected image data of the subject acquired by the transmission electron microscope, only over an area which is in a predetermined range from the calculated outline, wherein the image data generating unit generates the 3-dimensional image data by evenly distributing density of the projected image data of the subject only over an area which is in a predetermined range from the outline.

17. A computer executable program stored in a computer readable medium for image processing for acquiring 3-dimensional data of a subject by processing image data of the subject, said program comprising:

a shape computing unit operable to calculate shape data which represent a structural configuration of the subject, using projected image data of the subject acquired from a plurality of angles by a transmission electron microscope; and a first integrating unit operable to integrate projected image data of the subject acquired by the transmission electron microscope, on said shape data;

a distributing unit which generates gray-scale density-distributions by stretching and distributing densities shown in said projected image data respectively within angles along which said projected image data is captured;

a second integrating unit which generates 3-dimensional gray-scale data, which express the subject with 3-dimensional image data, by integrating a plurality of said gray-scale density-distributions generated from a plurality of said projected image data captured from a plurality of angles, wherein said first integrating unit integrates said 3-dimensional gray-scale data by said second integrating unit on said shape data; and a data processing unit which generates 3-dimensional image data by extracting only density which exists in perimeter of a shape that said shape data represent, from said 3-dimensional gray-scale data.

18. An image processing system for acquiring 3-dimensional data regarding a structural configuration of a subject by processing image data of the subject, comprising:

a transmission electron microscope for acquiring projected image data of the subject;

a shape computing unit which calculates shape data which represent an outline of the subject, using projected image data of the subject acquired from a plurality of angles by said transmission electron microscope;

a first integrating unit which integrates said projected image data of the subject acquired by said transmission electron microscope, on said shape data;

a distributing unit which generates gray-scale density-distributions by stretching and distributing densities shown in said projected image data respectively within angles along which said projected image data is captured;

a second integrating unit which generates 3-dimensional gray-scale data, which express the subject with 3-dimensional image data, by integrating a plurality of said gray-scale density-distributions generated from a plurality of said projected image data captured from a plurality of angles, wherein said first integrating unit integrates said 3-dimensional gray-scale data by said second integrating unit on said shape data; and a data processing unit which generates 3-dimensional image data by extracting only density which exists in perimeter of a shape that said shape data represent, from said 3-dimensional gray-scale data.

19. An image processing apparatus for acquiring 3-dimensional data regarding a structural configuration of a subject by processing image data of the subject, comprising:

a shape computing unit which calculates shape data which represent an outline of the subject, using projected image data of the subject acquired from a plurality of angles by a transmission electron microscope; and an image data generating unit which generates 3-dimensional image data by distributing density of the projected image data of the subject acquired by a transmission electron microscope, only over an area which is in a predetermined range from the calculated outline, wherein the image data generating unit generates the 3-dimensional image data by evenly distributing density of the projected image data of the subject only over an area which is in a predetermined range from the outline.

20. The image processing apparatus as claimed in claim 19, further comprising:

a gray-scale density data-generating unit which calculates from said 3-dimensional image data, said projected image data which should be acquired when the subject is captured from a different angle from said plurality of angles.

21. The image processing apparatus as claimed in claim 19, further comprising:

a sampling unit which extracts respectively projected image data of a plurality of said subjects facing a plurality of angles, included in a single projected image data acquired by the transmission electron microscope, wherein said image data generating unit uses a plurality of said projected image data which said sampling unit extracted.

22. The image processing apparatus as claimed in claim 19 wherein image data of the pattern of said subject are used as said projected image data.

23. The image processing apparatus as claimed in claim 19 wherein said shape computing unit includes:

a position relating unit which relates positions of processing object points in said subject in 1st and 2nd images which are consecutive in the order of angle, and relates the positions of the processing object points in said 2nd image and a 3rd image;

a height data computing unit which calculates height data for representing height of the position of said processing objective point using 2 sets of positions relation by said position relating unit; and a shape data computing unit which generates said shape data of said subject using said height data of a plurality of processing objective points calculated by said height data computing unit, wherein said apparatus calculates said shape data using three or more said 1st images.

24. An image processing method utilized by a processor for acquiring 3-dimensional data of a subject by processing image data of the subject, comprising steps of:

calculating an outline of the subject, using projected image data of the subject acquired from a plurality of angles by a transmission electron microscope; and generating 3-dimensional image data by distributing respectively density of the projected image data of the subject acquired by the transmission electron microscope, only over an area which is in a predetermined range from the calculated outline, wherein the generating generates the 3-dimensional image data by evenly distributing density of the projected image data of the subject only over an area which is in a predetermined range from the outline.

25. The image processing method as claimed in claim 24, further comprising steps of:

extracting projected image data of a plurality of said subjects facing a plurality of angles from a single projected image data acquired by the transmission electron microscope; and generating 3-dimensional image data by distributing respectively said extracted projected image data, around said outline.

26. The image processing method as claimed in claim 25, wherein said subject constitutes substance which has a helical symmetry, while said apparatus deals with projected image data of said substance as said single projected image data.

27. A computer executable program stored in a computer readable medium for image processing for acquiring 3-dimensional data of a subject by processing image data of the subject, said program comprising:

a shape computing unit operable to calculate an outline of the subject, using projected image data of the subject acquired from a plurality of angles by a transmission electron microscope; and an image data generating unit operable to generate 3-dimensional image data by distributing density of the projected image data of the subject acquired by the transmission electron microscope, only over an area which is in a predetermined range from the calculated outline, wherein the image data generating unit generates the 3-dimensional image data by evenly distributing density of the projected image data of the subject only over an area which is in a predetermined range from the outline.

28. An image processing system for acquiring 3-dimensional data regarding a structural configuration of a subject by processing image data of the subject, comprising:

a transmission electron microscope for acquiring projected image data of the subject;

a shape computing unit which calculates shape data which represent an outline of the subject, using projected image data of the subject acquired from a plurality of angles by said transmission electron microscope; and an image data generating unit which generates 3-dimensional image data by distributing density of said projected image data of the subject acquired by said transmission electron microscope, only over an area which is in a predetermined range from the calculated outline, wherein the image data generating unit generates the 3-dimensional image data by evenly distributing density of the projected image data of the subject only over an area which is in a predetermined range from the outline.

29. The image processing apparatus as claimed in claim 21, wherein said subject constitutes substance which has a helical symmetry, said apparatus dealing with projected image data of said substance as said single projected image data, further comprising:

an angle computing unit which acquires a reference angle, which is an angle the single subject as a reference faces, and further calculates angles which each of said subjects faces by adding or subtracting the angle which the helix rotates by said single subject to or from said reference angle.

* * * * *

UNITED STATES PATENT AND TRADEMARK OFFICE
CERTIFICATE OF CORRECTION

PATENT NO. : 7,639,865 B2 Page 1 of 1
APPLICATION NO. : 10/461920
DATED : December 29, 2009
INVENTOR(S) : Eisaku Katayama et al.

It is certified that error appears in the above-identified patent and that said Letters Patent is hereby corrected as shown below:

On the Title Page, item (62); Please insert -- the Domestic Priority Data of CON of PCT/JP01/1077 filed on December 10, 2001 and the Foreign Applications of JP2000-381636 filed on December 15, 2000 and JP2001-120262 filed on April 18, 2001 --

Signed and Sealed this

Tenth Day of August, 2010

David J. Kappos
*Director of the United States Patent and Trademark Office*